United States Patent
Du et al.

(10) Patent No.: US 7,393,331 B2
(45) Date of Patent: Jul. 1, 2008

(54) VORTEX BUBBLE-REMOVING AND COOLING SYSTEM FOR THE ELECTROMAGNETIC SHOCK WAVE GENERATOR FOR THE LITHOTRIPTER

(76) Inventors: Xixin Du, Room 401, Building No. 1, Yuebangercun, Yingchun Road, Wuzhong District, Suzhou City, Jiangsu Province (CN); Wolfgang Eisenmenger, Pfafferwaldring 57, D-70550 Stuttgart (DE)

(*) Notice: Subject to any disclaimer, the term of this patent is extended or adjusted under 35 U.S.C. 154(b) by 588 days.

(21) Appl. No.: 10/416,105

(22) PCT Filed: Nov. 2, 2001

(86) PCT No.: PCT/CN01/01526

§ 371 (c)(1),
(2), (4) Date: May 6, 2003

(87) PCT Pub. No.: WO02/051322

PCT Pub. Date: Jul. 4, 2002

(65) Prior Publication Data

US 2004/0015107 A1    Jan. 22, 2004

(30) Foreign Application Priority Data

Nov. 6, 2000    (CN) .................................. 00 1 19099

(51) Int. Cl.
*A61B 17/22* (2006.01)
(52) U.S. Cl. ............................. 601/4; 606/2.5; 367/167; 367/171
(58) Field of Classification Search ...................... 601/4; 606/2.5; 367/167, 171
See application file for complete search history.

(56) References Cited

U.S. PATENT DOCUMENTS

| 4,453,542 A | 6/1984 | Hughes |
| 4,530,358 A | 7/1985 | Forssmann et al. |
| 5,879,314 A * | 3/1999 | Peterson et al. ................ 601/2 |

FOREIGN PATENT DOCUMENTS

JP    2000-166869    6/2000

OTHER PUBLICATIONS

Nakayama et al. Correlation for Formation of Inlet Vortex. AIAA Journal 1999 0001-1452 vol. 37 No. 4 (508-510).*
Cole. Introduction to Classical Fluids or Divergence, Curl, and Other Things That Go Bump in the Night. Physics Department Learning Skills Center University of California, Davis. 1991-1998.*

* cited by examiner

*Primary Examiner*—Brian L. Casler
*Assistant Examiner*—Nasir S. Shahrestani
(74) *Attorney, Agent, or Firm*—Workman Nydegger

(57) ABSTRACT

The present invention relates to a vortex bubble removing and cooling system for the electromagnetic shock wave generator in the lithotripter. The vortex bubble-removing and cooling system comprises a water-full cushion (17), a metal diaphragm (14) installed inside the chamber body (27) of the water cushion (17) and a coil (13) which is installed at the backside of the metal diaphragm (14). There is at least one first water nozzle (22) on the side wall of the chamber body (27) and a water suction tube (23) at the center of the chamber body (27). The first water nozzle (22) and the water suction tube (23) form a vortex-generating device. The vortex generated inside the chamber body will scour the surface of the metal diaphragm continuously so as to cool the heat and remove the air bubble. This will make the metal diaphragm be in good working condition and greatly increase the working life of the metal diaphragm and the coil.

10 Claims, 3 Drawing Sheets

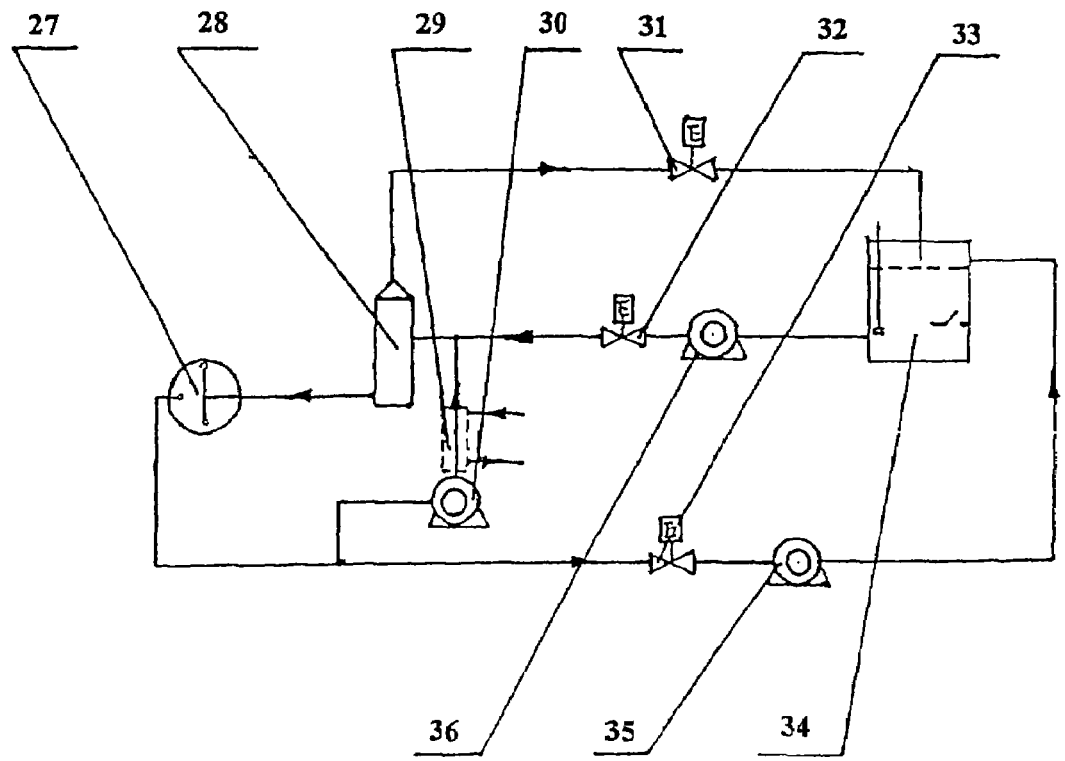
Fig 3
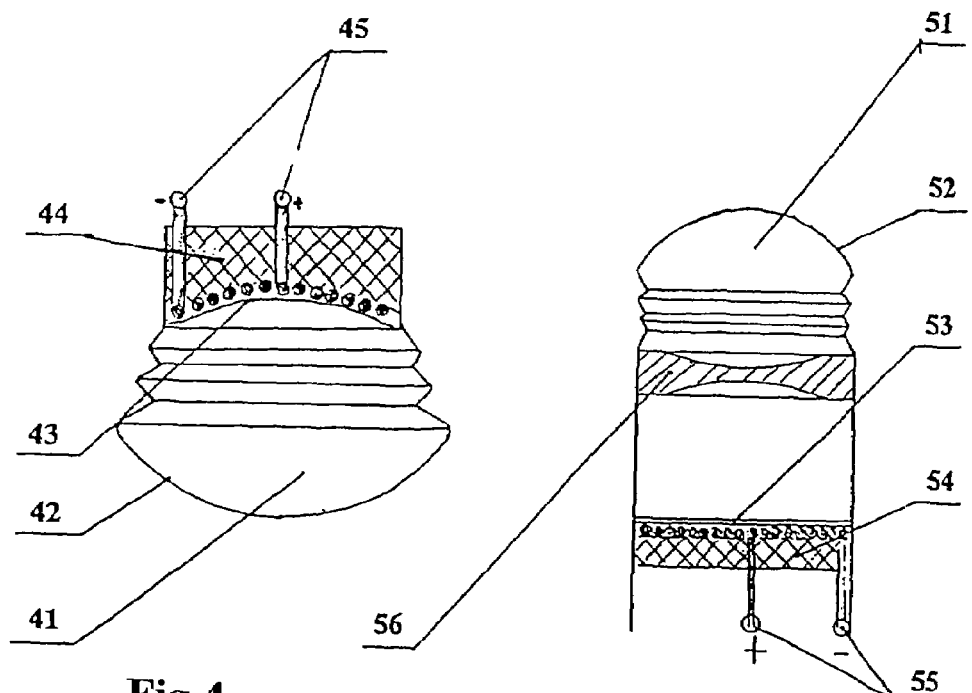
Fig 4
Fig 5

VORTEX BUBBLE-REMOVING AND COOLING SYSTEM FOR THE ELECTROMAGNETIC SHOCK WAVE GENERATOR FOR THE LITHOTRIPTER

TECHNICAL FIELD

The invention relates to a medical device, and more particularly to a lithotripter for fragmentation of stones in a human body.

BACKGROUND OF TECHNOLOGY

Conventionally, the electromagnetic shock wave lithotripter has types of shock wave sources: one is the incident focusing configuration, called self-focusing one, as shown in FIG. 4 and one of the others is the sound lens focusing configuration as shown in FIG. 5. The operation principle of the electromagnetic shock wave generator is as follows. When a strong pulse current passes through a coil, an induced current will be generated in a metal diaphragm. These two currents then form magnetic fields that repel each other, resulting in a sudden and short movement of the metal diaphragm. Consequently, a strong pressure pulse is generated in the nearby water. The pulse is gradually reinforced in propagation and thereby forms a shock wave.

With the incident focusing configuration shown in FIG. 4, the concave spherical coil will result in a concave spherical shock wave, which travels stably and keeps on focusing in propagation, therefore, without the need of the sound lens. With the sound lens-focusing configuration shown in FIG. 5, the planar coil will generate a planar shock wave. Therefore, the sound lens is required to focus the wave. In one stone fragmentation session, it is necessary to perform the high voltage pulse discharging for hundreds, or even thousands of times in order to disintegrate stone in the human body completely. Thus, a great amount of heat is produced in the coil. If the heat is not dissipated immediately, the metal diaphragm will be softened, destabilized and crumpled, thus the coil will be overheated and destroyed. Meanwhile, the interaction between the shock wave and the water will also result in cavitation and thus form bubbles in the water. The bubbles will adhere to the metal diaphragm, making the heat dissipation even worse. Further, when bubbles collapse under the interaction with the shock wave, micro-jets that can damage the metal diaphragm will be formed. Therefore, the conventional electromagnetic shock wave generator has a short working life, and it is necessary to replace the metal diaphragm very often. Accordingly, the configuration shown in FIG. 5 is often used in the prior art, wherein a metal diaphragm is placed over the coil, thereby the shock wave produced goes upward. In this way, the bubbles adhering to the metal diaphragm will moves upward under the action of the buoyancy force, and at the same time the heated water will also rise continuously, thus forming a fluid circulation in the chamber body. However, because the whole shock wave source is located in the lower part, it is inconvenient for physicians to move or locate it during treatment.

Therefore, it is an object of the invention to provide a vortex bubble-removing and cooling system for the electromagnetic shock wave generator for the lithotripter, which is capable of removing the bubbles adhering to a metal diaphragm automatically and dissipating the heat generated in the metal diaphragm immediately.

SUMMARY OF THE INVENTION

The invention provides a vortex bubble-removing and cooling system for the electromagnetic shock wave generator for the lithotripter, comprising a water cushion having a chamber body being filled with a liquid, the said water cushion embracing the housing of the generator;

a metal diaphragm disposed inside the chamber body; and a coil provided at the backside of the metal diaphragm;

wherein the chamber body located in front of the metal diaphragm has a circular cross section, at least one first water nozzle is set at the side wall of the chamber body. A water suction tube is set at the center of the chamber body, the first water nozzle and the water suction tube are communicated with a circulation system to maintain the amount of water in the chamber body at a constant level, i.e., the amount of water sprayed in is equal to the amount of water sucked away, the first water nozzle and the water suction tube form a vortex-generating device.

DESCRIPTION OF THE DRAWINGS

Hereinafter, the present invention will be further described with reference to the embodiments shown in the accompanying drawings, in which

FIG. 3 is a diagram illustrating a complete circulation system;

FIG. 4 illustrates a shock wave source of one conventional electromagnetic shock wave generator;

FIG. 5 illustrates a shock wave source of the conventional lens-focusing electromagnetic shock wave generator.

Figure 1:
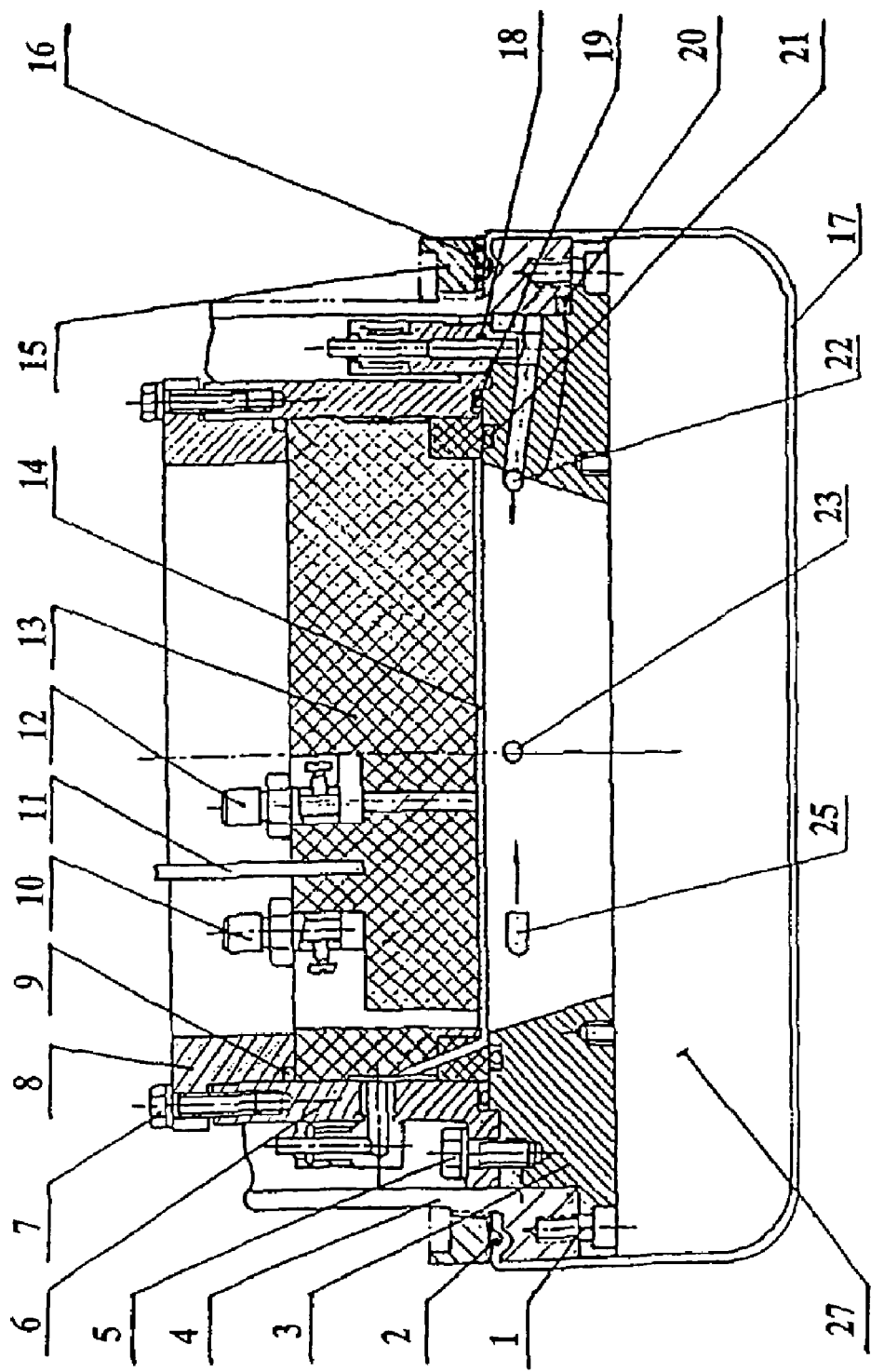
FIG. 1 is a main longitudinal-sectional view of the structure according to the invention.

The reference numerals used herein are as follows:

(1) bolt;
(2) sealing ring;
(3) base;
(4) connection cylinder;
(5) bolt;
(6) coil housing;
(7) bolt;
(8) coil cover;
(9) sealing ring;
(10) terminal;
(11) baffle;
(12) terminal;
(13) coil
(14) metal diaphragm;
(15) securing ring;
(16) washer
(17) water cushion;
(18) tube connector;
(19) sealing ring;
(20) sealing ring;
(21) sealing ring;
(22) first water nozzle;
(23) water suction tube;
(24) tube connector;
(25) second water nozzle;
(26) tube connector;
(27) chamber body;
(28) water and air separator;
(29) cooler;
(30) circulating pump;
(31) first solenoid valve;
(32) second solenoid valve
(33) third solenoid valve;
(34) water tank;
(35) water discharging pump;
(36) water charging pump;
(41) chamber body;
(42) water cushion;
(43) metal diaphragm;

(44) coil;
(45) terminal;
(51) chamber body;
(52) water cushion;
(53) metal diaphragm;
(54) coil;
(55) terminal;
(56) sound lens.

DETAILED DESCRIPTION OF THE EMBODIMENT

Referring to FIG. 1, the vortex bubble-removing and cooling system for the electromagnetic shock wave generator for the lithotripter according to the invention comprises a water cushion 17 having a chamber body 27, the chamber body 27 being filled with a water; a metal diaphragm 14 placed inside the chamber body 27; and a coil 13 provided at the backside of the metal diaphragm 14.

The chamber body 27 located in front of the metal diaphragm 14 has a circular cross section. At least one first water nozzle 22 for continuously spraying water is set on the side wall of the chamber body 27. A water suction tube 23 for continuously sucking water is set at the center of the chamber body 27. The first water nozzle 22 and the water suction tube 23 communicate with a circulation system. The first water nozzle 22 and the water suction tube 23 form a vortex-generating device which is capable of generating a vortex inside the chamber body 27.

The chamber body 27 is located below the metal diaphragm 14; therefore, the electromagnetic shock wave generator according to the invention can be positioned over a patient and is convenient for physicians to operate or locate.

Figure 2:
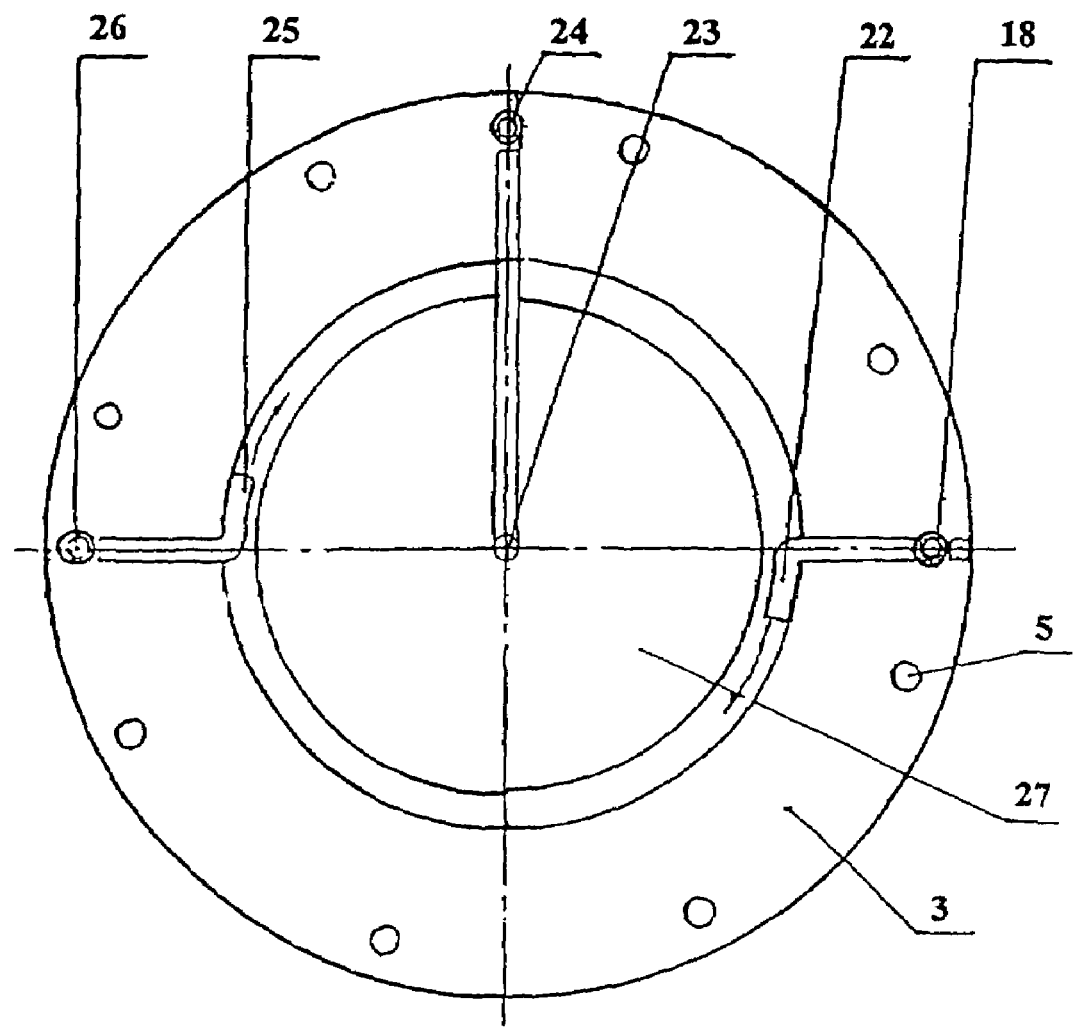
FIG. 2 is a cross-sectional view of a chamber body having a first water nozzle and a water suction tube.

Referring to FIG. 2, the first water nozzle 22 is parallel to the inner wall of the chamber body 27. The first water nozzle 22 is in the form of an arc concentric with the chamber body 27. A second water nozzle 25 symmetric to the first water nozzle 22 is also on the side wall of the chamber body 27. The second water nozzle 25 is communicated with the first water nozzle 22 using a pipe. Thus, both of the first and second water nozzles, which spray water along the inner wall of the chamber body, cooperate with the water suction tube 23 to generate a vortex. In the embodiment shown in FIG. 2, the second water nozzle 25 is oriented such that water that passes therethrough is directed into the chamber body 27 angled away from the water suction tube 23 so as to cause the water to rotate about the water suction tube 23 in the same rotational direction as the water from the first water nozzle 22. Furthermore, the first water nozzle 22 and the second water nozzle 25 are arranged to direct water into the chamber body 27 in a direction tangential to the side wall of the chamber body 27.

The water cushion 17 and the metal diaphragm 14 are fixed to the base 3, and the pipes connected to the first water spray nozzle 22 and the water suction tube 23 are all arranged on the base 3.

Referring to FIG. 3, a circulation system for use in a vortex bubble removing and cooling system for the electromagnetic shock wave generator for the lithotripter according to the invention is illustrated. The circulation system comprises a circulating pump 30. The water inlet of the circulating pump 30 is communicated with the water suction tube 23, while the water outlet of the circulating pump 30 is communicated with the first water nozzle 22 via the water-air separator 28. A water tank 34 is further provided in the circulation system to control the amount of water. The water tank 34 is connected to an air chamber of the water-air separator 28 via the first solenoid valve 31, thereby allowing the air carried into the water-air separator 28 to be released into the water tank. The water suction tube 23 is connected to the water tank 34 via a third solenoid valve 33 and a water-discharging pump 35. The water tank 34 is connected with the water-air separator 28 again via a pump 36 and a second solenoid valve 32. Further, a cooler 29 is connected in series with the inlet or outlet of the circulating pump 30.

The advantages of the present invention comparing with the prior art:

The water suction tube sucks water out of, while the first water nozzle sprays water into the chamber body continuously. Thus, a vortex is formed inside the chamber body. The vortex scours the surface of the metal diaphragm repeatedly so as to carry off the heat and bubbles, and concentrate them at the center. The heated water and the bubbles are continuously sucked away by the water suction tube, keeping the metal diaphragm in good working condition and greatly increasing the working life of the metal diaphragm and the coil.

What is claimed is:

1. A vortex bubble-removing and cooling system for an electromagnetic shock wave generator for a lithotripter, comprising
    a water cushion having a chamber body being filled with a cooling liquid;
    a metal diaphragm placed inside the said chamber body;
    at least one first nozzle adapted to direct the liquid into the chamber body in such a way that a vortex is created in the chamber body by the liquid directed from the first nozzle, whereby bubbles are removed from a surface of the metal diaphragm and forced to a center of the chamber body; and
    at least one intake tube provided at the center of the chamber body for taking the liquid and bubbles out of the chamber body;
    wherein the chamber body has a circular cross section, and the first nozzle is adapted to direct the liquid into the chamber body in a tangential direction of an inner wall of the chamber body.

2. The vortex bubble-removing and cooling system for an electromagnetic shock wave generator for a lithotripter according to claim 1, further comprising a first pipe where an outlet of the first nozzle is formed, wherein the first pipe abuts against the inner wall of the chamber body.

3. The vortex bubble-removing and cooling system for an electromagnetic shock wave generator for a lithotripter according to claim 1, further comprising a second nozzle arranged symmetrically to the first nozzle.

4. The vortex bubble-removing and cooling system for an electromagnetic shock wave generator for a lithotripter according to claim 1, wherein the liquid is water.

5. The vortex bubble removing and cooling system for an electromagnetic shock wave generator for a lithotripter according to claim 1, wherein the intake tube is a suction tube that takes the liquid and bubbles out of the chamber body by a suction, and wherein the first nozzle and the intake tube communicate with a circulation system.

6. The vortex bubble-removing and cooling system for an electromagnetic shock wave generator for a lithotripter according to claim 5, wherein the circulation system comprises a circulating pump having an inlet and an outlet, the inlet of the circulating pump communicating with the shock wave generator through the suction tube and the outlet of the circulating pump communicating with a liquid air separator, and the liquid air separator communicating with the shock wave generator through a pipe connecting the liquid air separator to the first nozzle.

7. The vortex bubble removing and cooling system for an electromagnetic shock wave generator for a lithotripter according to claim 6, wherein the circulation system further includes a liquid tank which communicates with an air chamber of the liquid air separator via a first solenoid valve, and wherein the suction tube communicates with the liquid tank via a third solenoid valve and a liquid discharging pump, and wherein the liquid tank communicates with the liquid air separator via a liquid charging pump and a second solenoid valve.

8. A vortex bubble-removing and cooling system for an electromagnetic shock wave generator for a lithotripter, comprising
   a water cushion having a chamber body, the chamber body being filled with a liquid;
   a metal diaphragm placed inside the chamber body; and
   a coil provided at a backside of the said metal diaphragm;
   wherein a portion of the chamber body is located in front of the metal diaphragm and has a circular cross section, and wherein at least one first water nozzle is set at a side wall of the chamber body and a water suction tube is set at a center of the chamber body, the first water nozzle and the water suction tube communicating with a circulation system, and wherein the first water nozzle is oriented such that water that passes therethrough is directed into the chamber body angled away from the water suction tube so as to cause the water to rotate around the water suction tube in a rotational direction and thereby create a vortex;
   wherein said system further comprises a second water nozzle and a second pipe disposed where the second water nozzle is formed, the second water nozzle being symmetric to the first water nozzle and being provided at the side wall of the said chamber body, wherein the second pipe communicates with the first pipe;
   wherein the second water nozzle is oriented such that water that passes therethrough is directed into the chamber body angled away from the water suction tube so as to cause the water to rotate about the water suction tube in the same rotational direction as the water from the first water nozzle; and
   wherein the first water nozzle and the second water nozzle are arranged to direct water into the chamber body in a direction tangential to the side wall of the chamber body.

9. The vortex bubble-removing and cooling system for an electromagnetic shock wave generator for a lithotripter according to claim 8, further comprising a first pipe disposed where an outlet of the first water nozzle is formed, wherein the first pipe abuts against an inner wall of the chamber body, and the first water nozzle is in the form of an arc concentric with the chamber body.

10. The vortex bubble-removing and cooling system for an electromagnetic shock wave generator for a lithotripter according to claim 1, further comprising a coil provided at a backside of the metal diaphragm, wherein the chamber body is located in front of the metal diaphragm, and the first nozzle is set at a side wall of the chamber body.

* * * * *